United States Patent [19]

Mueller et al.

[11] Patent Number: 4,827,035

[45] Date of Patent: * May 2, 1989

[54] PREPARATION OF AMINES

[75] Inventors: Herbert Mueller, Frankenthal; Hartmut Axel, Schwetzingen, both of Fed. Rep. of Germany

[73] Assignee: BASF Aktiengesellschaft, Ludwigshafen, Fed. Rep. of Germany

[*] Notice: The portion of the term of this patent subsequent to Apr. 10, 2001 has been disclaimed.

[21] Appl. No.: 9,040

[22] Filed: Jan. 23, 1987

Related U.S. Application Data

[63] Continuation of Ser. No. 815,788, Jan. 3, 1986, which is a continuation of Ser. No. 560,118, Dec. 12, 1983.

[30] Foreign Application Priority Data

Dec. 18, 1982 [DE] Fed. Rep. of Germany ....... 3246978

[51] Int. Cl.$^4$ .............................................. C07C 85/06
[52] U.S. Cl. .................................... 564/402; 564/447; 564/479
[58] Field of Search .................. 564/479, 402, 447

[56] References Cited

U.S. PATENT DOCUMENTS

| | | | |
|---|---|---|---|
| 2,953,601 | 9/1960 | Whitaker | 260/585 |
| 3,223,734 | 12/1965 | Fallstad et al. | 260/583 |
| 3,708,539 | 1/1973 | Fenton | 260/585 B |
| 4,210,605 | 7/1980 | Hoshino et al. | 564/479 |
| 4,254,060 | 3/1981 | Kimura et al. | 564/479 |
| 4,442,306 | 4/1984 | Mueller et al. | 564/479 |

FOREIGN PATENT DOCUMENTS

| | | |
|---|---|---|
| 2255701 | 5/1974 | Fed. Rep. of Germany . |
| 2625196 | 3/1980 | Fed. Rep. of Germany . |
| 3128889 | 2/1983 | Fed. Rep. of Germany . |

OTHER PUBLICATIONS

Russian Chemical Reviews, 34 (1965) 843.
Spialter et al, Process Evaluation and Research Planning Service, Report 1978, Chem. System, New York, p. 429.
L. Spialter and J. A. Rappalardo, "The Acyclic Aliphatic Tertiary Amines", The Macmillan Comp., 1965.

Primary Examiner—Charles F. Warren
Assistant Examiner—Carolyn S. Greason
Attorney, Agent, or Firm—Keil & Weinkauf

[57] ABSTRACT

Primary, secondary and tertiary amines are prepared by reacting ammonia or a primary amine with a primary or secondary monohydric or polyhydric alcohol over a copper catalyst such as that which forms of its own accord from copper formate under the reaction conditions.

9 Claims, No Drawings

PREPARATION OF AMINES

This application is a continuation of application Ser. No. 815,788, filed on Jan. 3, 1986, which is a continuation application Ser. No. 560,118, filed on Dec. 12, 1983.

The invention relates to a novel process for the preparation of primary, secondary or tertiary amines by reacting ammonia or a primary amine with an alcohol over a copper-containing catalyst.

Catalytic alkylation of ammonia or an amine with an alcohol using a dehydrating oxide, eg. an oxide of aluminum, thorium, tungsten or chromium, as the catalyst has been disclosed. Hydrogenation and dehydrogenation catalysts with the active metals copper, nickel or cobalt or noble metals have also been recommended for this purpose. The hydrogenation/dehydrogenation catalysts are solids and are used in the form of a suspension, if they are powdered, or in the form of shaped pieces if they are used as a fixedbed catalyst. Liquid phase and gas phase processes have been proposed. This specialist field is given a detailed description in a paper by V. A. Nekrasova and N. I. Shuikin in the journal Russian Chemical Reviews, 34 (1965) 843 and in the book "The acyclic aliphatic tertiary amines", L. Spialter and J. A. Rappalardo, The Macmillan Comp., 1965.

It is particularly difficult to prepare amines in which different alkyl radicals are linked to the nitrogen. Primary, secondary and tertiary amines with an undesirable alkyl group distribution are formed as by-products as a result of transalkylation reactions, and frequently can be separated off from the desired reaction products only with a very great deal of effort. These transalkylation reactions are particularly prominent when hydrogenation/dehydrogenation catalysts of inadequate activity are used.

The catalysts to be used for alkylating ammonia or primary amines with alcohol are known from many publications. They are in all cases metallic catalysts which are either prepared outside the reaction system and activated or formed by reduction at the start of the catalysis.

U.S. Pat. No. 2,953,601 describes the use of Raney nickel or nickel precipitated on aluminum for this purpose. The Examples show that the values for the conversion and yield of these reactions are not satisfactory.

According to the proposal of U.S. Pat. No. 3,223,734, Raney nickel, copper/chromium oxide, palladium-on-carbon or nickel-on-diatomaceous-earth can be used as the catalyst for the preparation of amines. However, as the Examples of the patent show, favorable results cannot be achieved with these catalysts either, and, furthermore, uneconomically large amounts are frequently consumed.

U.S. Pat. No. 3,708,539 discloses an improved process for the preparation of amines. In this process, an alcohol is reacted, in the liquid phase, with a secondary amine over a ruthenium, osmium, rhenium or technetium catalyst. The particular disadvantage of this process is the fact that the conversion and yield, based on the alcohols employed and measured by the value of the raw catalyst materials, are unsatisfactory for an industrial process.

Japanese Preliminary Published Application No. 19604/77 discloses a substantially improved method for the preparation of dimethyldodecylamine in a yield of about 90% using a copper/chromium oxide catalyst on diatomaceous earth.

German Laid-Open Application DOS No. 2,255,701 discloses a process for the preparation of secondary amines from alcohol and ammonia by suspension catalysis. It is found that it is very difficult to avoid the formation of tertiary amines in this reaction, and that the secondary amines can be formed in a yield of over 80% only if an excess of ammonia in the reaction system is prevented by substantial technical effort.

German Laid-Open Applications DOS No. 2,907,869 and DOS No. 3,005,953 therefore disclose a quasi-homogeneous colloidal catalyst system which does not have the above disadvantages of solid catalysts. These colloidal catalysts are formed when a mixture of carboxylic acid salts of copper or silver with carboxylic acid salts of elements of group VIII of the periodic table (including manganese and zinc) and carboxylic acid salts of the alkali metal and alkaline earth metal elements is reduced with hydrogen or aluminum alkyl compounds. Inner complexes of, for example, dicarbonyl compounds can also be used instead of salts of carboxylic acids.

As is generally known from other aminolysis reactions, a good activity and selectivity are achieved with these catalysts only if a combination of several active metals in the correct proportions is used. Another disadvantage is that the catalysts must be activated before the actual reaction by reduction with hydrogen or aluminum-alkyls. Finally, the catalysts cannot be removed mechanically in a simple manner, but must be separated off by distillation of the reaction product. The catalyst thus remains in the higher-boiling or non-distillable residues simultaneously formed. Although the catalysts can initially be used for another reaction, a continuous increase in the level of byproducts in the reaction system is unavoidable as a result. Apart from the fact that the survival of sensitive substances during distillation in the presence of catalytically active metals is poor and these substances can suffer modification, there is also the problem of removing these catalysts from the residues at a later point in time without causing pollution.

It is an object of the present invention to prepare aliphatic and cycloaliphatic amines and aralkylamines by a route which permits a high yield of the desired products, produces few contaminating by-products and requires only minimal use of a catalyst. The catalyst to be used should permit the preparation of primary, secondary or tertiary amines, as desired. In addition, substantially complete conversion of the alcohols should occur, since later removal of the alcohols from the desired product is frequently difficult. Finally, after the reaction, the nature of the catalyst should be such that it can easily be removed quantitatively from the reaction product and used for further reactions, and the formation of residues, higher molecular weight condensates and side reactions should be substantially excluded. This versatile catalyst must moreover be formed from a simple, readily accessible range of chemicals and if possible become active directly for the reaction without requiring its own activation step.

We have found that this object is achieved and that primary and symmetric or asymmetric secondary and tertiary amines with a total of not more than about 40 carbon atoms are prepared in an advantageous manner by reacting ammonia or a primary amine with a primary or secondary monohydric or polyhydric alcohol, in particular an alcohol of 6 or more carbon atoms, over a copper catalyst at from 170° to 250° C. in the presence or absence of hydrogen by a process wherein a catalyst such as is formed of its own accord from copper formate under the reaction conditions is used.

German Laid-Open Application DOS No. 3,128,889 discloses a similar process for the preparation of tertiary amines, starting from secondary amines.

As in that Application, a conventional procedure is also advantageously followed here, in which ammonia or the particular primary amine is added to the liquid reaction mixture containing the particular alcohol at a rate corresponding to the reaction, and water is removed at a rate corresponding to its formation.

The process according to the invention is chiefly used for reacting high-boiling alcohols with ammonia or the particular primary amine. (If a high-boiling primary amine is alkylated with a low-boiling alcohol, it is advantageous to add the alcohol to the liquid reaction mixture containing the amine at a rate corresponding to the reaction and to remove the water at a rate corresponding to its formation.)

This process can be carried out, for example, by adding the copper formate to the alcohol (or the amine) and heating the mixture in the presence or absence of small amounts of amine (alcohol). The intended reaction usually starts of its own accord at about 170° C. Under these conditions, the catalyst displays its maximum catalytic action, without prior additional activation.

The nitrogen component to be alkylated can be added by means of a metering device to the alcohol, which has been brought to the reaction temperature. This procedure is preferred if the reaction temperature is above the boiling point of the amine component to be used and the reaction is carried out under isobaric conditions. The accumulation of relatively large and excessive amounts of amine is thus avoided, which has an advantageous effect on the yield.

In the case of a batchwise procedure, the reaction is thus usually carried out with gradual addition of the ammonia or the primary amine until the alcohol has been consumed, and the amine formed can then be obtained by distillation of the liquid reaction mixture.

In an appropriate modification, in a continuous operation, for example, gaseous ammonia or primary amine is passed in cocurrent or countercurrent to the liquid reaction mixture containing the alcohol, the suspended catalyst and, where relevant, the amine formed in the reaction. If necessary, an after-reaction zone should be provided here.

An important measure for achieving optimum results is continuous removal from the reaction mixture of the water formed, which means that the reaction is advantageously carried out under conditions under which water leaves the reaction mixture of its own accord as a vapor.

For understanding of the invention, the following may be said: if the reaction takes place in the vapor phase, a very high reaction temperature must be chosen, since the alcohols generally have a relatively low volatility; a low yield and impure products are then obtained. On the other hand, if the reaction is carried out in the liquid phase, for example—in the case of highly volatile amines, such as ethylamine—by applying a high pressure, taking into consideration the temperature, and using a high concentration of amine, the course of the reaction is highly non-specific. The amount of water, which usually increases with the conversion, also acts in this sense.

The reaction conditions disclosed in German Laid-Open Application DOS No. 2,625,196 are advantageously followed. By using copper formate as the catalyst, it is possible under those conditions to manage with substantially smaller amounts of catalyst, to obtain purer products and to apply the reaction also to the preparation of secondary amines. At the same time, higher yields are also achieved.

It is also advantageous to carry out the reaction in the presence of, for example, from 0.1 to 50% by weight, preferably from 1 to 10% by weight (based on the copper catalyst), of a base, such as an alkali metal hydroxide or alkaline earth metal hydroxide, eg. sodium hydroxide, potassium hydroxide or calcium hydroxide, or particularly advantageously the corresponding carbonate; several of the above compounds can be present at once.

The reaction can in fact be carried out in the absence of hydrogen—according to the overall equation. Thus, for example, the reaction between an alcohol and ammonia proceeds of its own accord through addition of the ammonia gas to the reaction mixture, as soon as the required reaction temperature is reached. The desired amine is obtained in a yield of from 90 to 95%, with an alcohol conversion of more than 99% Nevertheless, in some cases it has proven advantageous to add small amounts of hydrogen to the reaction medium, and in certain circumstances this promotes the activity of the catalyst and prevents formation of small amounts of unsaturated compounds. However, if the reaction is carried out in the absence of hydrogen and small amounts of unsaturated compounds are thereby formed, it is advisable to hydrogenate these when the amination has ended.

No particular requirements are imposed on the nature and properties of the copper formate. For example, commercially available copper formate containing water of crystallization can be used, without pretreatment. Anhydrous copper formate can, however, also be used with the same result. The manner in which the copper salt has been prepared is of no significance for its catalytic activity. For example, a suitable catalyst is obtained if the formate is prepared from copper oxide, hydroxide, stearate or carbonate and formic acid. This reaction can also be carried out in the absence of water, for example with the copper compound and formic acid in the alcohol intended for the aminolysis reaction. Finally, it is also possible simply to mix aqueous copper formate solution, as the catalyst intermediate, with the alcohol. The water introduced into the reaction medium is distilled off, even before the reaction temperature is reached during the heating-up step. It can be assumed that the actual catalyst forms of its own accord as a result of reaction of copper formate with constituents in the reaction mixture. The amount of copper formate required to achieve adequate conversion and a sufficiently high rate of reaction is from 0.01 to 2% by weight, preferably from 0.05 to 1% by weight (calculated as metallic copper), based on the sum of the feed substances. Since virtually none of the catalyst formed from the copper formate is consumed when pure starting materials are used and the catalyst can be used over and over, its low costs are of no importance. Thus, the catalysts can be removed at any time and converted back into copper formate and, if desired, used again, after renewed addition of a basic alkali metal compound or alkaline earth metal compound.

The alcohol used as the starting material can contain a linear or branched, saturated or unsaturated aliphatic hydrocarbon chain, the carbon chain of which can be interrupted by heteroatoms, in particular oxygen. Although secondary alcohols can be reacted by the present process, the reaction with primary alcohols is preferred. The best results are therefore obtained with monofunctional or polyfunctional primary alcohols of 2 or more carbon atoms.

Target products which are particularly important industrially are the fatty amines; these are derived from alcohols of from about 6 to 22 carbon atoms in the molecule (fatty alcohols). Examples are octyl alcohol, lauryl alcohol, myristyl alcohol, cetyl alcohol, oleyl alcohol, stearyl alcohol, tridecyl alcohol, pentadecyl alcohol and mixtures of these compounds.

Other examples of suitable alcohols are dihydric alcohols, such as ethylene glycol, diethylene glycol, butane-1,4-diol and hexane-1,6-diol.

In the process according to the invention, alcohols of not more than 6 carbon atoms are chiefly used for the preparation of asymmetric secondary or tertiary amines; the primary amine used as the starting substance should contain not less than 8 carbon atoms (i.e. should be an amine of low volatility). With these lower alcohols, there is furthermore the possibility of using the corresponding polyhydric alcohols of low volatility.

It is also possible to use, instead of the alcohols, linear or branched, saturated or unsaturated aliphatic aldehydes, such as lauric aldehyde, or oxoaldehydes, which are reduced to alcohols in the presence of hydrogen under the reaction conditions.

Primary amines which, besides ammonia, are suitable for the process according to the invention contain alkyl, cycloalkyl or aralkyl substituents of, for example, 1 to 18 or more carbon atoms, preferably 1 to 16 and in particular 1 to 12 carbon atoms. Examples of industrially important primary amines are methylamine, propylamine, octylamine, decylamine and laurylamine.

The reaction is generally carried out at from 170° to 250° C., preferably from 180° to 220° C., under atmospheric, superatmospheric or reduced pressure, for example in a range from 10 mbar to 6 bar, the pressure range to be chosen also depending on the properties of the participating reactants and the chosen reaction temperature.

If a high-boiling alcohol, for example decanol, lauryl alcohol or tridecyl alcohol, is used for the alkylation, it is sufficient to heat the alcohol in the presence of the copper formate, with or without the addition of the activating alkali metal compound, and to pass ammonia or the primary amine into the reation mixture at a rate corresponding to its reaction. The water formed during the reaction is continuously distilled off from the system. This last operation can be promoted by removing the water of reaction from the system as an azeotrope with a suitable solvent, for example an aliphatic or aromatic hydrocarbon, and separating it off. A reactor equipped with a stirring apparatus, a condenser and a water separator is therefore an example of a suitable reaction chamber. A particularly simple method thus comprises bringing the alcohol to the reaction temperature and adding ammonia or the primary amine and, where relevant, hydrogen. The water formed is removed in vaporous form from the reaction zone and condensed, and the gas which has not been consumed is fed back. Not more than the equimolar amount per hour of the amine, preferably from 0.3 to 0.6 mole of the amine per mole of alcohol, can be passed into the reaction mixture, depending on the reaction temperature and the amount of catalyst. The amount of hydrogen which may be used is of the same order of size or even substantially lower. It can in any case be varied within wide limits.

From the preceding statements, it can be seen that the reaction conditions are advantageous if it is possible to carry out the reaction in the course of about 1 to 10 hours. Shorter reaction times are not to be recommended, because of the amount of heat which has to be supplied to the water of reaction to be evaporated. In contrast, longer reaction times are acceptable, with no adverse effect on the reaction. Furthermore, the rate of reaction is of course always determined by the amount of amine added per unit time. It is usually chosen so that the concentration of ammonia or primary amine remains constant at a few per cent of the reaction mixture, ie., averaged out over a period of time, the alcohol is preferably used in a large excess in comparison with the amine.

A particular result of the invention is that, after complete conversion and mechanical removal of the catalyst, the reaction products are usually sufficiently pure for many fields of use, without further purification operations. The products are always colorless and are usually contaminated by less than 5% by weight of by-products.

This means that purification by distillation can be omitted, especially in the preparation of high-boiling tertiary amines (for example trioctylamine, which is used as an extracting agent for ores), and a not insignificant amount of energy is thus saved. In comparison with the procedure disclosed in German Laid-Open Application DOS No. 2,907,869, apart from the advantages mentioned above, it should be noted that the alkylation starts at substantially lower temperatures. The reaction temperature in the process according to the invention is on average from 10° to 20° C. lower. This is one of the principal reasons for the high selectivity achieved in the process according to the invention.

The high selectivity in the preparation of secondary amines starting from ammonia is particularly surprising, since it is known that alkylamines are very much more reactive than ammonia in their reaction with alcohols (Process Evaluation and Research Planning Service, Report 1978, published by Chem. System, New York, page 429, last section).

Since an object of the process according to the invention is, inter alia, to convert the alcohol completely, not less than the stoichiometric amount in total of ammonia or the primary amine will be available. A certain excess of a highly volatile amine or ammonia may be advantageous towards the end of the reaction. This excess may be on average from 5 to 50 mole %, preferably from 10 to 20 mole %, i.e., where relevant, the conversion conditions are maintained until an appropriate conversion can be expected. Ammonia or primary amine available in excess is then removed again. It is important to add the ammonia or primary amine during the reaction at a rate corresponding to its reaction. According to the invention, this means that the alcohol is present in excess throughout the entire duration of the reaction, ie. as long as it is still present in a noticeable concentration in the reaction mixture. Such reaction conditions are very easy to achieve in a countercurrent process, which can moreover be operated as a continuous procedure.

The Examples which follow illustrate the invention:

EXAMPLE 1

5,200 kg of n-octan-1-ol, 100 kg of copper formate (Cu(HCOO)$_2$).4H$_2$O), 500 kg of n-octylamine and 10 kg of calcium hydroxide were introduced into a stirred apparatus under atmospheric pressure, and were heated to 180° C. while 10 m³ of hydrogen/hour were passed in. The mixture was stirred at this temperature for 1 hour; the temperature was then increased to 200° C., during which ammonia was fed in.

240 kg of ammonia were then added to the reaction system in the course of 10 hours, about 5% of this amount being removed as waste gas.

While about 70 kg/hour of ammonia were converted in the initial phase, this conversion rate fell to less than 1 kg/hour towards the end of the reaction. Distillation and quantitative gas chromatography of a representative sample taken showed the following product yields, based on the alcohol employed:

| Tri-n-octylamine | 94% of theory |
| Di-n-octylamine | 2% of theory |
| n-Octylamine | 1% of theory |
| n-Octan-1-ol | 0.5% of theory |

(The octylamine initially added was taken into consideration in the calculation of the yields.)

A distillation residue of 2% by weight, based on the alcohol employed, remained.

The catalyst was separated off from the reaction batch completely, by centrifugation, and was recycled to the stirred reactor, where it was used for further reactions. For this, a further 5 kg of copper formate and 1 kg of calcium hydroxide were added to the stirred container before each new batch, and the amination was then carried out as described above. It was possible to carry out 10 aminations in this manner without a noticeable drop in the rate of reaction or selectivity.

When the reaction was carried out without the addition of calcium hydroxide, a reaction time of about 40 hours was required for complete conversion of the alcohol. The yield of tri-n-octylamine, however, was only from 88 to 90% of theory, based on the amount of alcohol employed.

When the calcium hydroxide was replaced by barium hydroxide or potassium carbonate, the tri-n-octylamine was obtained in a yield of about 93% of theory. While addition of calcium oxide produced a slightly poorer result, doping of the catalyst with sodium carbonate or sodium bicarbonate increased the rate of reaction by about 20%.

EXAMPLE 2

8,000 kg of n-decan-1-ol, 360 kg of copper formate and 40 kg of calcium hydroxide were introduced into a stirred apparatus under atmospheric pressure, and were heated to 180° C.

At the same time, a mixture consisting of 6 parts by volume of ammonia and 1 part by volume of hydrogen was introduced under the surface of the reaction mixture. 480 kg of ammonia were added to the mixture in this manner at 180° C. in the course of 13 hours, about 10% of this amount being removed as waste gas.

After this time, the removal of water, which took place simultaneously, had virtually ended. The reaction mixture was kept at the above temperature, without addition of ammonia or hydrogen, for a further 3 hours. After cooling, the catalyst was separated off and the clear reaction mixture was distilled. Quantitative analysis of the reaction mixture by gas chromatography showed that conversion, in this manner, of the n-decan-1-ol employed was as follows: from 88 to 90 mole % into di-n-decylamine from 10 to 12 mole % into tri-n-decylamine and about 2 mole % into n-decylamine.

A distillation residue of 1% by weight, based on the alcohol employed, remained.

EXAMPLE 3

8,000 kg of n-decan-1-ol, 200 kg of copper formate and 50 kg of calcium hydroxide were introduced into a stirred apparatus under atmopheric pressure. The reaction system was rapidly heated to 200° C., while a mixture initially consisting of 8 parts by volume of methylamine and 1 part by volume of hydrogen was passed in. Methylamine was added in an amount such that the total amount was just reacted and about 10% thereof was removed as waste gas, while the amount of hydrogen passed in was kept constant over the entire reaction time at 5 m³/hour.

1,300 kg of methylamine were passed in over a period of 17 hours in this manner.

Since the amine number of the reaction mixture was 236 mg of KOH/g, a further 2,550 kg of n-decan-1-ol had to be added. Stirring was then continued at the above temperature for a further 8 hours, while the mixture was gassed with hydrogen. After cooling, the catalyst was removed and the mixture was worked up by distillation.

The crude product, the amine number of which was 172 mg of KOH/g (calculated value for methyl di-n-decylamine equals 180 mg of KOH/g), had the following composition:

| Methyl di-n-decylamine | 93% by weight |
| Methyl-n-decylamine | 3% by weight |
| n-Decan-1-ol | 0.1% by weight |
| Non-volatile constituents | 4% by weight |

EXAMPLE 4

150 kg of 2-hydroxydecahydronaphthalene, 3 kg of copper formate and 2 kg of calcium hydroxide were gassed at 190° C. with excess ammonia and hydrogen (volume ratio of 8:1) for 4 hours. The supply of ammonia was then discontinued and the mixture was gassed with just hydrogen at the reaction temperature for a further 2 hours. Working up was carried out in the conventional manner. Bis(decahydronaphthyl)amine was obtained in a yield of 98% of theory.

EXAMPLE 5

The catalyst which remained after the reaction described in Example 1 had been carried out was freed from the adhering amine by washing with tetrahydrofuran and used for the prepration of butyldodecylamine.

5,000 kg of dodecylamine were heated to from 190° to 200° C., together with the catalyst, in the apparatus described in Example 1, and about 200 kg of butanal and 10 m³ of hydrogen per hour were added. The water of reaction formed in the alkylation and excess butanal were passed through a dephlegmator operated at 100° C., and were then condensed, the condensate separating into two phases. The lower aqueous phase was discarded, while the upper phase, which consisted substantially of butanal, was recycled to the reaction.

After 10 hours, no further water of reaction was obtained, the reaction was interrupted and the reaction product was cooled. According to analysis by gas chromatography, the reaction product contained: 80% by weight of butyldodecylamine 11.5% by weight of dibutyldodecylamine from 1 to 1.5% by weight of starting substances from 5 to 7% by weight of higher-boiling constituents The end products can be obtained in a pure form by distillation.

We claim:

1. A process for the preparation of a primary or symmetric or asymmetric secondary or tertiary amine with a total of not more than about 40 carbon atoms which comprises: reacting ammonia or a primary amine with a primary or secondary monohydric or polyhydric alcohol over a copper catalyst at from 170° to 250° C. in the presence or absence of hydrogen, said catalsyt being formed from copper formate under the reaction conditions.

2. The process of claim 1, wherein the reaction is carried out in the presence of a basic alkali metal or alkaline earth metal compound.

3. The process of claim 1, wherein ammonia or a primary amine is added to the liquid reaction mixture containing the alcohol, at a rate corresponding to the reaction, and water is removed at a rate corresponding to its formation.

4. The process of claim 1, wherein ammonia or a highly volatile primary amine is added in vaporous form.

5. The process of claim 1, wherein ammonia or a primary amine is added to the reaction mixture at a temperature above the particular boiling point of this amino component, and the reaction is carried out under constant pressure.

6. The process of claim 1, wherein, in the case of a batchwise procedure, the reaction is carried out until the alcohol is consumed and the amine formed is isolated from the liquid reaction mixture by distillation.

7. The process of claim 1, wherein, in the case of a continuous procedure, ammonia or a highly volatile primary amine is passed in gaseous form in countercurrent to the liquid reaction mixture containing the alcohol and, if appropriate, the amine formed.

8. The process of claim 1, wherein the catalyst which has been separated off from the reaction product is used again for further reactions, if appropriate after renewed addition of a basic alkali metal or alkaline earth metal compound.

9. The process of claim 1, wherein the alcohol has 6 or more carbon atoms.

* * * * *

UNITED STATES PATENT AND TRADEMARK OFFICE
CERTIFICATE OF CORRECTION

PATENT NO. : 4,827,035
DATED : May 2, 1989
INVENTOR(S) : MUELLER, Herbert; AXEL, Hartmut; WITTWER, Arnold It is certified that error appears in the above-identified patent and that said Letters Patent is hereby corrected as shown below:

Title page:

Missing from inventors

Third Inventor - "Arnold WITTWER, Ludwigshafen"

Signed and Sealed this

Seventeenth Day of October, 1989

Attest:

DONALD J. QUIGG

Attesting Officer

Commissioner of Patents and Trademarks